United States Patent [19]
Gibson et al.

[11] Patent Number: 5,811,120
[45] Date of Patent: Sep. 22, 1998

[54] SOLID ORALLY ADMINISTERABLE RALOXIFENE HYDROCHLORIDE PHARMACEUTICAL FORMULATION

[75] Inventors: Lowell L. Gibson, Greenwood; Kerry J. Hartauer; Julian L. Stowers, both of Indianapolis; Stephanie A. Sweetana, Bloomington; Arvind L. Thakkar, Indianapolis, all of Ind.

[73] Assignee: Eli Lilly and Company, Indianapolis, Ind.

[21] Appl. No.: 824,590

[22] Filed: Mar. 26, 1997

Related U.S. Application Data

[63] Continuation of Ser. No. 479,585, Jun. 7, 1995, abandoned, which is a continuation of Ser. No. 204,915, Mar. 2, 1994, abandoned.

[51] Int. Cl.$^6$ .......................... A61K 9/20; A61K 31/445
[52] U.S. Cl. .......................... 424/464; 424/451; 424/463; 424/474; 424/490; 514/960; 514/962; 514/324
[58] Field of Search .......................... 424/451, 463, 424/464, 474, 490, 484, 48; 514/962, 960, 324

[56] References Cited

U.S. PATENT DOCUMENTS

| | | | |
|---|---|---|---|
| 4,133,814 | 1/1979 | Jones | 260/326.55 |
| 4,418,068 | 11/1983 | Jones | 424/267 |
| 4,797,286 | 1/1989 | Thakkar et al. | 424/456 |
| 4,847,092 | 7/1989 | Thakkar et al. | 424/456 |
| 5,112,619 | 5/1992 | Thakkar et al. | 424/456 |
| 5,461,064 | 10/1995 | Cullinan | 514/324 |
| 5,462,950 | 10/1995 | Fontana | 514/324 |
| 5,510,370 | 4/1996 | Hock | 514/443 |

FOREIGN PATENT DOCUMENTS 2101356  1/1994  Canada .

OTHER PUBLICATIONS van Hoogdalem et al., Pharmac. Ther., 44, 407 (1989).

Dissolution, Bioavailability, and Bioequivalende, Mack Publishing Company, (1989), Chapter 5, *Factors Affecting the Rate of Dissolution of Solid Dosage Forms.*

*Primary Examiner*—Raj Bawa
*Attorney, Agent, or Firm*—James J. Sales; Steven P. Caltrider; David E. Boone

[57] ABSTRACT

This invention provides solid orally administerable pharmaceutical formulations comprising raloxifene hydrochloride, a surfactant being sorbitan fatty acid ester or a polyoxyethylene sorbitan fatty acid ester, polyvinylpyrrolidone, and a water soluble diluent which is polyol or sugar.

33 Claims, No Drawings

SOLID ORALLY ADMINISTERABLE RALOXIFENE HYDROCHLORIDE PHARMACEUTICAL FORMULATION

This application is a continuation application Ser. No. 08/479,585, filed Jun. 7, 1995, which is a file-wrapper-continuing of application Ser. No. 08/204,915, filed Mar. 2, 1994, abandoned.

BACKGROUND

Certain benzothiophenes of the formula

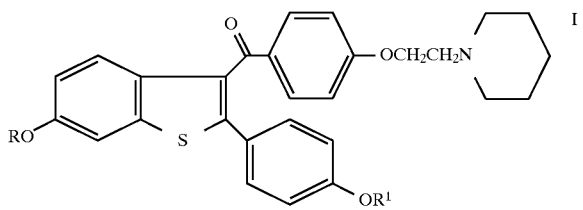

wherein R and $R^1$ are independently hydrogen, $COR^2$, or $R^3$;
$R^2$ is hydrogen, $C_1$–$C_{14}$ alkyl, $C_1$–$C_3$ chloroalkyl, $C_1$–$C_3$ fluoroalkyl, $C_5$–$C_7$ cycloalkyl, $C_1$–$C_4$ alkoxy, phenyl, or phenyl mono- or disubstituted with $C_1$–$C_4$ alkyl, $C_1$–$C_4$ alkoxy, hydroxy, nitro, chloro, fluoro, or tri(chloro or fluoro)methyl;
$R^3$ is $C_1$–C4 alkyl, $C_5$–$C_7$ cycloalkyl, or benzyl; or
a pharmaceutically-acceptable salt thereof; are nonsteriodal antiestrogens and antiandrogens. These compounds are useful in the treatment of mammary and prostatic tumors, and in the treatment of mammary and prostatic fibrocystic disease. The formula I compounds are described in U.S. Pat. No. 4,418,068 (issued Nov. 29, 1983). This patent described the preparation of these compounds, as well as their use for antiestrogen and antiandrogen therapy. The preparation of pharmaceutical compositions for antiestrogenic and antiandrogenic therapy was also described.

Raloxifene, which is 6-hydroxy-2-(4-hydroxyphenyl)-3-[4-(2-piperidinoethoxy)benzoyl]benzo[b]thiophene, is a particulary useful compound from this series of benzothiophenes. Raloxifene competitively inhibits estrogen action in a number of in vitro and in vivo models. Black, Jones, and Falcone, *Life Sci.*, 32, 1031–1036 (1983); Knecht, Tsai-Morris, and Catt, *Endocrinology*, 116, 1771–1777 (1985); and Simard and Labrie, *Mol. Cell. Endocrinology*, 39, 141–144 (1985). This compound also displays some estrogen-like actions in addition to its estrogen-antagonistic effects. Ortmann, Emons, Knuppen, and Catt, *Endocrinology*, 123, 962–968 (1988). A recent report suggests that raloxifene is useful in the treatment of osteoporosis in postmenopausal women. Turner, Sato, and Bryant, *Journal of Clinical Investigation* (In Press).

The formula I compounds may be administered as pharmaceutically-acceptable salts. A particularly useful pharmaceutically-acceptable salt of raloxifene is the hydrochloride salt. This salt form is easily prepared by the addition of hydrogen chloride to a solution of raloxifene in an organic solvent, such as tetrahydrofuran or methanol. Aqueous solubility of raloxifene hydrochloride, however, is far below what would be expected for an organic hydrochloride salt containing two phenolic hydroxyl groups. This poor solubility has somewhat limited the bioavailability of this preferred salt form. Another significant barrier to optimum and consistent absorption of raloxifene hydrochloride is its hydrophobicity.

SUMMARY OF THE INVENTION

To overcome the limited bioavailability, the present invention provides orally administerable pharmaceutical formulations comprising raloxifene, its esters or ethers, or a pharmaceutically-acceptable salt thereof, in combination with a hydrophilic carrier composition, such formulations having increased solubility in aqueous media. More particularly, the present invention provides an orally administerable pharmaceutical formulation comprising raloxifene, its esters or ethers, or a pharmaceutically-acceptable salt thereof, in combination with a surfactant, a water-soluble diluent, and optionally a hydrophilic binder. The present invention also provides pharmaceutical formulations further comprising a lubricant and a disintegrant.

DETAILED DESCRIPTION OF THE INVENTION

The present invention provides orally administerable pharmaceutical formulations comprising raloxifene, its esters or ethers, or a pharmaceutically-acceptable salt thereof, in combination with a surfactant, a water-soluble diluent, and optionally a hydrophilic binder. Raloxifene, its esters, and its ethers are represented by the following formula:

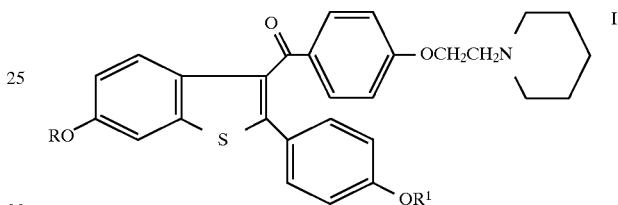

wherein R and $R^1$ are independently hydrogen, $COR^2$, or $R^3$;
$R^2$ is hydrogen, $C_1$–$C_{14}$ alkyl, $C_1$–$C_3$ chloroalkyl, $C_1$–$C_3$ fluoroalkyl, $C_5$–$C_7$ cycloalkyl, $C_1$–$C_4$ alkoxy, phenyl, or phenyl mono- or disubstituted with $C_1$–$C_4$ alkyl, $C_1$–$C_4$ alkoxy, hydroxy, nitro, chloro, fluoro, or tri(chloro or fluoro)methyl;
$R^3$ is $C_1$–$C_4$ alkyl, $C_5$–$C_7$ cycloalkyl, or benzyl. Raloxifene is the compound wherein R and $R^1$ are hydrogen. The preparation of this compound is described in U.S. Pat. No. 4,418,068, which is incorporated herein by reference. A pharmaceutical chemist will readily recognize that this compound can be effectively administered as an ether or ester, formed on either one or both of the phenolic hydroxyl groups. The preparation of these esters and ethers is also described in U.S. Pat. No. 4,418,068.

The general chemical terms used in the above formula have their usual meanings. The term "$C_1$–$C_{14}$ alkyl" represents a straight or branched alkyl chain having from one to 14 carbon atoms. Typical $C_1$–$C_{14}$ alkyl groups include methyl, ethyl, n-propyl, isopropyl, n-butyl, isobutyl, sec-butyl, t-butyl, n-pentyl, isopentyl, n-hexyl, 2-methylpentyl, n-octyl, decyl, 2-methyldecyl, 2,2-dimethyldecyl, undecyl, dodecyl, and the like. The term "$C_1$–$C_{14}$ alkyl" includes within it the term "$C_1$–$C_4$ alkyl". Typical $C_1$–$C_4$ alkyl groups include methyl, ethyl, n-propyl, isopropyl, n-butyl, isobutyl, sec-butyl, and t-butyl.

The terms "$C_1$–$C_3$ chloroalkyl" and "$C_1$–$C_3$ fluoroalkyl" represent methyl, ethyl, propyl, and isopropyl substituted to any degree with chlorine or florine atoms, from one atom to full substitution. Typical $C_1$–$C_3$ chloroalkyl groups include chloromethyl, dichloromethyl, trichloromethyl, 2-chlorethyl, 2,2-dichloroethyl, 2,2,2-trichloroethyl, 1,2-dichloroethyl, 1,1,2,2-tetrachloroethyl, 1,2,2,2-tetrachloroethyl, pentachlorethyl, 3-chloropropyl, 2-chloropropyl, 3,3-dichloropropyl, 2,3-dichloropropyl, 2,2-dichloropropyl, 3,3,3-trichloropropyl, and 2,2,3,3,3-pentachloropropyl. Typical $C_1$–$C_3$ fluoroalkyl groups include fluoromethyl, difluoromethyl, trifluoromethyl, 2-fluoroethyl, 2,2-difluoroethyl, 2,2,2-trifluoroethyl, 1,2-difluoroethyl, 1,1,2,2-tetrafluoroethyl, 1,2,2,2-tetrafluoroethyl, pentafluoroethyl, 3-fluoropropyl, 2-fluoropropyl, 3,3-difluoropropyl, 2,3-difluoropropyl, 2,2-difluoropropyl, 3,3,3-trifluoropropyl, and 2,2,3,3,3-pentafluoropropyl.

The term "$C_5$–$C_7$ cycloalkyl" represents cyclic hydrocarbon groups containing from five to seven carbon atoms. The $C_5C_7$ cycloalkyl groups are cyclopentyl, cyclohexyl, and cycloheptyl.

The term "$C_1$–$C_4$ alkoxy" represents groups such as methoxy, ethoxy, n-propoxy, isopropoxy, n-butoxy, t-butoxy, and the like groups.

The term "pharmaceutically-acceptable salt" represents salt forms of raloxifene, its esters, or its ethers that are physiologically suitable for pharmaceutical use. The pharmaceutically-acceptable salts can exist in conjunction with raloxifene, its esters, or its ethers as acid addition primary, secondary, tertiary, or quaternary ammonium, alkali metal, or alkaline earth metal salts. Generally, the acid addition salts are prepared by the reaction of an acid with a compound of formula I, wherein R, $R^1$, $R^2$, and $R^3$, are as defined previously. The alkali metal and alkaline earth metal salts are generally prepared by the reaction of the metal hydroxide of the desired metal salt with a compound of formula I, wherein at least one of R and $R^1$ is hydrogen.

Acids commonly employed to form such acid addition salts include organic acids such as hydrochloric, hydrobromic, hydriodic, sulfuric, and phosphoric acid, as well as organic acids such as toluenesulfonic, methanesulfonic, oxalic, para-bromophenylsulfonic, carbonic, succinic, citric, benzoic, and acetic acid, and related inorganic and organic acids. Such pharmaceutically-acceptable salts thus include sulfate, pyrosulfate, bisulfate, sulfite, bisulfite, phosphate, ammonium, monohydrogen phosphate, dihydrogen phosphate, meta-phosphate, pyrophosphate, chloride, bromide, iodide, acetate, propionate, decanoate, caprolate, acrylate, formate, isobutyrate, caprate, heptanoate, propionate, oxalate, malonate, succinate, subarate, sebacate, fumarate, hippurate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, α-hydroxybutyrate, glycolate, tartrate, methanesulfonate, propanesulfonate, naphthalene-1-sulfonate, naphthalene-2-sulfonate, mandelate, ammonium, magnesium, tetramethylammonium, potassium, trimethylammonium, sodium, methylammonium, calcium, and the like salts.

The term "hydrophilic binder" represents binders commonly used in the formulation of pharmaceuticals, such as polyvinylpyrrolidone, polyethylene glycol, sucrose, dextrose, corn syrup, polysaccharides (including acacia, tragacanth, guar, and alginates), gelatin, and cellulose derivatives (including hydroxypropyl methylcellulose, hydroxypropyl cellulose, and sodium carboxymethylcellulose).

The term "surfactant", as used herein, represents ionic and nonionic surfactants or wetting agents commonly used in the formulation of pharmaceuticals, such as ethoxylated castor oil, polyglycolyzed glycerides, acetylated monoglycerides, sorbitan fatty acid esters, poloxamers, polyoxyethylene sorbitan fatty acid esters, polyoxyethylene derivatives, monoglycerides or ethoxylated derivatives thereof, diglycerides or polyoxyethylene derivatives thereof, sodium docusate, sodium laurylsulfate, cholic acid or derivatives thereof, lecithins, and phospholipids.

The term "water-soluble diluent" represents compounds typically used in the formulation of pharmaceuticals, such as sugars (including lactose, sucrose, and dextrose), polysaccharides (including dextrates and maltodextrin), polyols (including mannitol, xylitol, and sorbitol), and cyclodextrins.

The term "disintegrant" represents compounds such as starches, clays, celluloses, alginates, gums, cross-linked polymers (such as cross-linked polyvinylpyrrolidone and cross-linked sodium carboxymethylcellulose), sodium starch glycolate, low-substituted hydroxypropyl cellulose, and soy polysaccharides. Preferably the disintegrant is a cross-linked polymer, more preferably cross-linked polyvinylpyrrolidone.

The term "lubricant" represents compounds frequently used as lubricants or glidants in the preparation of pharmaceuticals, such as talc, magnesium stearate, calcium stearate, stearic acid, colloidal silicon dioxide, magnesium carbonate, magnesium oxide, calcium silicate, microcrystalline cellulose, starches, mineral oil, waxes, glyceryl behenate, polyethylene glycol, sodium benzoate, sodium acetate, sodium chloride, sodium laurylsulfate, sodium stearyl fumarate, and hydrogenated vegetable oils. Preferably the lubricant is magnesium stearate or stearic acid, more preferably magnesium stearate.

While all of the formulations of the present invention have increased solubility in aqueous media and, therefore, greater bioavailability would be expected, certain formulations are preferred. Preferably, the surfactant is an anionic or nonionic surfactant. Representative surfactants from this preferred group include sodium laurylsulfate, sodium docusate, ethoxylated castor oil, polyglycolyzed glycerides, acetylated monoglycerides, sorbitan fatty acid esters, poloxamers, polyoxyethylene sorbitan fatty acid esters, polyoxyethylene derivatives, monoglycerides or ethoxylated derivatives thereof, and diglycerides or polyoxyethylene derivatives thereof. Preferably, the water-soluble diluent is a sugar or polyol. When a hydrophilic binder is present, preferably the binder is sucrose, dextrose, corn syrup, gelatin, a cellulose derivative, or polyvinylpyrrolidone.

Certain formulations of the present invention are more preferred. More preferably, the surfactant is a nonionic surfactant, such as ethoxylated castor oil, polyglycolyzed glycerides, acetylated monoglycerides, sorbitan fatty acid esters, poloxamers, polyoxyethylene sorbitan fatty acid esters, polyoxyethylene derivatives, monoglycerides or ethoxylated derivatives thereof, and diglycerides or polyoxyethylene derivatives thereof. More preferably, the water-soluble diluent is a sugar, such as lactose, sucrose, and dextrose. More preferably, the hydrophilic binder is a cellulose derivative or polyvinylpyrrolidone.

Certain formulations of the present invention are most preferred. Most preferably, the surfactant is a polyoxyethylene sorbitan fatty acid ester, such as polysorbate 80. Most preferably, the water-soluble diluent is lactose. Most preferably the hydrophilic binder, when present, is polyvinylpyrrolidone.

The orally administerable compositions of the present invention are prepared and administered according to methods well known in pharmaceutical chemistry. See Remington's Pharmaceutical Sciences, 17th ed. (A. Osol ed., 1985). For example, the compositions of the present invention may be adminstered by means of solid dosage forms such as tablets and capsules. Preferably, the compositions are formulated as tablets. These tablets are prepared by wet granulation, by dry granulation, or by direct compression.

Tablets for this invention are prepared utilizing conventional tabletting techniques. A general method of manufacture involves blending raloxifene, its ester, ether, or a salt thereof, the water-soluble diluent, and optionally a portion of a disintegrant. This blend is then granulated with a solution of the hydrophilic binder and surfactant in water and/or organic solvent, such as methanol, ethanol, isopropanol, methylene chloride, and acetone, and milled if necessary. The granules are dried and reduced to a suitable size. Any other ingredients, such as lubricants, (e.g. magnesium stearate) and additional disintegrant, are added to the granules and mixed. This mixture is then compressed into a suitable size and shape using conventional tabletting machines such as a rotary tablet press. The tablets may be film coated by techniques well known in the art.

Capsules for this invention are prepared utilizing conventional encapsulating methods. A general method of manufacture involves blending raloxifene, its ester, ether, or salt thereof, the water-soluble diluent, and optionally a portion of a disintegrant. This blend is then granulated with a solution of the hydrophilic binder and surfactant in water and/or organic solvent, and milled if necessary. The granules are dried and reduced to a suitable size. Any other ingredients, such as a lubricant (e.g. colloidal silicon dioxide) are added to the granules and mixed. The resulting mixture is then filled into a suitable size hard-shell gelatin capsule using conventional capsule-filling machines.

The following formulation examples are illustrative only and are not intended to limit the scope of the invention in any way. Tablets may be prepared using the ingredients and procedures as described below:

Formulation 1

| Ingredient | Weight (mg/tablet) |
| --- | --- |
| Raloxifene HCl | 200.00 |
| Polyvinylpyrrolidone | 15.75 |
| Polysorbate 80 | 5.25 |
| Lactose Anhydrous | 264.62 |
| Cross-linked polyvinylpyrrolidone | 31.50 |
| Stearic Acid | 5.25 |
| Magnesium Stearate | 2.63 |

The mixture of raloxifene HCl lactose, and a portion of the cross-linked polyvinylpyrrolidone is granulated with an aqueous solution of the polyvinylpyrrolidone and polysorbate 80. The granules are dried, reduced to a suitable size, and mixed with stearic acid, magnesium stearate, and remaining cross-linked polyvinylpyrrolidone. The mixture is compressed into individual tablets yielding a tablet weight of 525 mg.

Formulation 2

| Ingredient | Weight (mg/tablet) |
| --- | --- |
| Raloxifene HCl | 200.00 |
| Polyvinylpyrrolidone | 15.75 |
| Polysorbate 80 | 5.75 |
| Lactose Anhydrous | 132.06 |
| Dextrose | 132.06 |
| Cross-linked polyvinylpyrrolidone | 31.50 |
| Stearic acid | 5.25 |
| Magnesium Stearate | 2.63 |

The mixture of raloxifene HCl lactose anhydrous, dextrose, and a portion of the cross-linked polyvinylpyrrolidone is granulated with an alcoholic solution of polyvinylpyrrolidone and polysorbate 80. The granules are dried, reduced to a suitable size, and mixed with magnesium stearate, stearic acid, and remaining cross-linked polyvinylpyrrolidone. The mixture is compressed into individual tablets yielding a tablet weight of 525 mg.

Formulation 3

| Ingredient | Weight (mg/tablet) |
| --- | --- |
| Raloxifene HCl | 200.00 |
| Hydroxypropyl Cellulose | 16.00 |
| Sodium Laurylsulfate | 10.00 |
| Dextrose | 154.00 |
| Cross-linked sodium carboxymethylcellulose | 16.00 |
| Magnesium Stearate | 4.00 |

The mixture of raloxifene HCl, dextrose, and cross-linked sodium carboxymethylcellulose is granulated with an aqueous solution of hydroxypropyl cellulose and sodium laurylsulfate. The granules are dried, reduced to a suitable size, and mixed with magnesium stearate. The mixture is compressed into individual tablets yielding a tablet weight of 400 mg.

Formulation 4

| Ingredient | Weight (mg/tablet) |
| --- | --- |
| Raloxifene HCl | 30.00 |
| Lactose Anhydrous | 144.00 |
| Lactose, Hydrous spray Dried | 36.00 |
| Polyvinylpyrrolidone | 12.00 |
| Polysorbate 80 | 2.40 |
| Cross-linked polyvinylpyrrolidone | 14.40 |
| Magnesium Stearate | 1.20 |

The mixture of raloxifene HCl lactose anhydrous, spray-dried hydrous lactose, and a portion of the cross-linked polyvinylpyrrolidone is granulated with an aqueous solution of polyvinylpyrrolidone and polysorbate 80. The granules are dried, reduced to a suitable size, and mixed with magnesium stearate and remaining cross-linked polyvinylpyrrolidone. The mixture is compressed into individual tablets yielding a tablet weight of 240 mg.

Formulation 5

| Ingredient | Weight (mg/tablet) |
| --- | --- |
| Raloxifene HCl | 30.00 |
| Lactose Anhydrous | 160.00 |
| Hydroxypropyl Cellulose | 11.00 |
| Poloxamer | 7.00 |
| Cross-linked sodium carboxymethylcellulose | 23.00 |
| Stearic Acid | 7.00 |
| Magnesium Stearate | 2.00 |

The mixture of raloxifene HCl, anhydrous lactose, and cross-linked sodium carboxymethylcellulose is granulated with an aqueous solution of poloxamer and hydroxypropyl cellulose. The granules are dried, reduced to a suitable size, and mixed with stearic acid and magnesium stearate. The mixture is then compressed into individual tablets yielding a tablet weight of 240 mg.

| Formulation 6 | |
|---|---|
| Ingredient | Weight (mg/tablet) |
| Raloxifene HCl | 30.00 |
| Lactose | 89.00 |
| Dextrose | 89.00 |
| Hydroxypropyl methylcellulose | 10.00 |
| Sodium Laurylsulfate | 5.00 |
| Cross-linked polyvinylpyrrolidone | 12.00 |
| Stearic Acid | 5.00 |

The mixture of raloxifene HCl lactose, dextrose, and cross-linked polyvinylpyrrolidone is granulated with an aqueous solution of hydroxypropyl methylcellulose and sodium laurylsulfate. The granules are dried, reduced to a suitable size, and mixed with the stearic acid. The mixture is then compressed into individual tablets yielding a tablet weight of 240 mg.

| Formulation 7 | |
|---|---|
| Ingredient | Weight (mg/tablet) |
| Raloxifene HCl | 60.00 |
| Lactose Anhydrous | 156.00 |
| Polyvinylpyrrolidone | 7.20 |
| Polysorbate 80 | 7.20 |
| Cross-linked polyvinylpyrrolidone | 7.20 |
| Magnesium Stearate | 2.40 |

The mixture of raloxifene HCl, lactose anhydrous, and cross-linked polyvinylpyrrolidone is granulated with an aqueous solution of polyvinylpyrrolidone and polysorbate 80. The granules are dried, reduced to a suitable size, and mixed with magnesium stearate. The mixture is then compressed into individual tablets yielding a tablet weight of 240 mg.

| Formulation 8 | |
|---|---|
| Ingredient | Weight (mg/tablet) |
| Raloxitene HCl | 60.00 |
| Lactose Anhydrous | 120.00 |
| Lactose, hydrous spray-dried | 30.00 |
| Polyvinylpyrrolidone | 12.00 |
| Polysorbate 80 | 2.40 |
| Cross-linked polyvinylpyrrolidone | 14.40 |
| Magnesium Stearate | 1.20 |

The mixture of raloxifene HCl, lactose anhydrous, spray-dried hydrous lactose, and a portion of the cross- linked polyvinylpyrrolidone is granulated with an aqueous solution of polyvinylpyrrolidone and polysorbate 80. The granules are dried, reduced to a suitable size, and mixed with magnesium stearate and remaining cross-linked polyvinylpyrrolidone. The mixture is then compressed into individual tablets yielding a tablet weight of 240 mg.

| Formulation 9 | |
|---|---|
| Ingredient | Weight (mg/tablet) |
| Raloxifene HCl | 60.00 |
| Mannitol | 77.00 |
| Dextrose | 73.00 |
| Hydroxypropyl methylcellulose | 7.00 |
| Polysorbate 80 | 4.00 |
| Sodium Starch Glycolate | 14.00 |
| Stearic Acid | 4.00 |
| Magnesium Stearate | 1.00 |

The mixture of raloxifene HCl mannitol, dextrose, and sodium starch glycolate is granulated with an aqueous solution of polysorbate 80 and hydroxypropyl methylcellulose. The granules are dried, reduced to a suitable size, and mixed with stearic acid and magnesium stearate. The mixture is then compressed into individual tablets yielding a tablet weight of 240 mg.

| Formulation 10 | |
|---|---|
| Ingredient | Weight (mg/tablet) |
| Raloxifene HCl | 150.00 |
| Lactose, anhydrous | 41.00 |
| Lactose, hydrous spray dried | 10.25 |
| Polyvinylpyrrolidone | 11.50 |
| Polysorbate 80 | 2.30 |
| Cross-linked polyvinylpyrrolidone | 13.80 |
| Magnesium Stearate | 1.15 |

The mixture of raloxifene HCl, anhydrous lactose, hydrous spray-dried lactose, and a portion of the cross-linked polyvinylpyrrolidone is granulated with an aqueous solution of polyvinylpyrrolidone and polysorbate 80. The granules are dried, reduced to a suitable size, and mixed with magnesium stearate and the remaining cross-linked polyvinylpyrrolidone. The mixture is then compressed into individual tablets yielding a tablet weight of 230 mg.

| Formulation 11 | |
|---|---|
| Ingredient | Weight (mg/tablet) |
| Raloxifene HCl | 150.00 |
| Lactose, hydrous spray-dried | 56.00 |
| Polyvinylpyrrolidone | 7.00 |
| Polysorbate 80 | 1.20 |
| Cross-linked polyvinylpyrrolidone | 13.80 |
| Magnesium Stearate | 2.00 |

The mixture of raloxifene HCl, hydrous spray-dried lactose, and a portion of the cross-linked polyvinylpyrrolidone is granulated with an aqueous solution of polyvinylpyrrolidone and polysorbate 80. The granules are dried, reduced to a suitable size and mixed with magnesium stearate and remaining cross-linked polyvinylpyrrolidone. The mixture is then compressed into individual tablets yielding a tablet weight of 230 mg.

| Formulation 12 | |
|---|---|
| Ingredient | Weight (mg/tablet) |
| Raloxifene HCl | 150.00 |
| Lactose, anhydrous | 52.40 |
| Polysorbate 80 | 4.60 |
| Polyvinylpyrrolidone | 11.50 |
| Polyethylene Glycol 8000 | 11.50 |

The mixture of raloxifene HCl and anhydrous lactose is granulated with an aqueous solution of polysorbate 80 and polyvinylpyrrolidone. The granules are dried, reduced to a suitable size, and mixed with the polyethylene glycol 8000. The mixture is then compressed into individual tablets yielding a tablet weight of 230 mg.

Capsules may be prepared using the ingredients and procedures as described below:

| Formulation 13 | |
|---|---|
| Ingredient | Weight (mg/capsule) |
| Raloxifene HCl | 30.00 |
| Lactose, hydrous spray-dried | 178.30 |
| Sodium laurylsulfate | 4.60 |
| Cross-linked polyvinylpyrrolidone | 9.20 |
| Hydroxypropyl methylcellulose | 6.90 |
| Colloidal Silicon Dioxide | 1.00 |

The mixture of raloxifene HCl, hydrous spray-dried lactose, and cross-linked polyvinylpyrrolidone is granulated with an aqueous solution of sodium laurylsulfate and hydroxypropyl methylcellulose. The granules are dried, reduced to a suitable size, and mixed with colloidal silicon dioxide. This mixture is then filled into Size 3 hard-shell gelatin capsules utilizing conventional encapsulating equipment, with each capsule containing 230 mg of the final mixture.

| Formulation 14 | |
|---|---|
| Ingredient | Weight (mg/capsule) |
| Raloxifene HCl | 60.00 |
| Lactose, hydrous spray-dried | 148.30 |
| Sodium laurylsulfate | 4.60 |
| Cross-linked polyvinylpyrrolidone | 9.20 |
| Hydroxypropyl methylcellulose | 6.90 |
| Colloidal Silicon Dioxide | 1.00 |

The mixture of raloxifene HCl, hydrous spray-dried lactose, and cross-linked polyvinylpyrrolidone is granulated with an aqueous solution of sodium laurylsulfate and hydroxypropyl methylcellulose. The granules are dried, reduced to a suitable size, and mixed with colloidal silicon dioxide. This mixture is then filled into Size 3 hard-shell gelatin capsules utilizing conventional encapsulating equipment, with each capsule containing 230 mg of the final mixture.

| Formulation 15 | |
|---|---|
| Ingredient | Weight (mg/capsule) |
| Raloxifene HCl | 150.00 |
| Lactose, hydrous spray-dried | 58.30 |
| Sodium laurylsulfate | 4.60 |
| Cross-linked polyvinylpyrrolidone | 9.20 |
| Hydroxypropyl methylcellulose | 6.90 |
| Colloidal Silicon Dioxide | 1.00 |

The mixture of raloxifene HCl, hydrous spray-dried lactose, and cross-linked polyvinylpyrrolidone is granulated with an aqueous solution of sodium laurylsulfate and hydroxypropyl methylcellulose. The granules are dried, reduced to a suitable size, and mixed with colloidal silicon dioxide. This mixture is then filled into Size 3 hard-shell gelatin capsules utilizing conventional encapsulating equipment, with each capsule containing 230 mg of the final mixture.

We claim:

1. A solid administerable pharmaceutical formulation comprising raloxifene hydrochloride in combination with a surfactant, polyvinylpyrrolidone, and a water soluble diluent, wherein:
    the surfactant is a sorbitan fatty acid ester or a polyoxyethylene sorbitan fatty acid ester; and
    the water soluble diluent is a polyol or sugar.

2. The formulation of claim 1, wherein the surfactant is a polyoxyethylene sorbitan fatty acid ester.

3. The formulation of claim 2, wherein the surfactant is polysorbate 80.

4. The formulation of claim 1, wherein the water soluble diluent is a sugar.

5. The formulation of claim 4, wherein the surfactant is polyoxyethylene sorbitan fatty acid ester.

6. The formulation of claim 5, wherein the sugar is lactose.

7. The formulation of claim 6, wherein the surfactant is polysorbate 80.

8. The formulation of claim 7 further comprising a lubricant and a disintegrant.

9. The formulation of claim 1 further comprising a lubricant and a disintegrant.

10. The formulation of claim 9, wherein the lubricant is magnesium stearate or stearic acid, and the disintegrant is cross-linked polyvinylpyrrolidone.

11. The formulation of claim 10, wherein the surfactant is polyoxyethylene sorbitan fatty acid ester.

12. The formulation of claim 11, wherein the diluent is a sugar.

13. A solid administerable pharmaceutical formulation consisting essentially of raloxifene hydrochloride in combination with a surfactant, polyvinylpyrrolidone, and a water soluble diluent, wherein:
    the surfactant is a sorbitan fatty acid ester or a polyoxyethylene sorbitan fatty acid ester; and
    the water soluble diluent is polyol or sugar.

14. The formulation of claim 13, wherein the surfactant is polyoxyethylene sorbitan fatty acid ester.

15. The formulation of claim 14, wherein the diluent is a sugar.

16. A solid administerable pharmaceutical formulation consisting essentially of raloxifene hydrochloride in combination with polysorbate 80, lactose, polyvinylpyrrolidone, and magnesium stearate.

17. The formulation of claim 8, further comprising a film coating.

18. The formulation of claim 12, further comprising a film coating.

19. The formulation of claim 15, further comprising a film coating.

20. The formulation of claim 16, further comprising a film coating.

21. The formulation of claim 1 wherein said formulation is in the form of a tablet or capsule.

22. The formulation of claim 3 wherein said formulation is in the form of a tablet or capsule.

23. The formulation of claim 8 wherein said formulation is in the form of a tablet or capsule.

24. The formulation of claim 10 wherein said formulation is in the form of a tablet or capsule.

25. The formulation of claim 12 wherein said formulation is in the form of a tablet or capsule.

26. The formulation of claim 13 wherein said formulation is in the form of a tablet or capsule.

27. The formulation of claim 14 wherein said formulation is in the form of a tablet or capsule.

28. The formulation of claim 15 wherein said formulation is in the form of a tablet or capsule.

29. The formulation of claim 16 wherein said formulation is in the form of a tablet or capsule.

30. The formulation of claim 17 wherein said formulation is in the form of a tablet or capsule.

31. The formulation of claim 18 wherein said formulation is in the form of a tablet or capsule.

32. The formulation of claim 19 wherein said formulation is in the form of a tablet or capsule.

33. The formulation of claim 20 wherein said formulation is in the form of a tablet or capsule.

* * * * *

UNITED STATES PATENT AND TRADEMARK OFFICE
CERTIFICATE OF CORRECTION

PATENT NO.  : 5,811,120

DATED       : September 22, 1998

INVENTORS   : Lowell L. Gibson, et al.

It is certified that an error appears in the above-identified patent and that said Letters Patent is hereby corrected as shown below:

Column 1, line 26, please replace the term "$C_1$-C4 alkyl" with the following term -- $C_1$-$C_4$ alkyl --.

Column 3, line 10, please replace the term "$C_5C_7$ cycloalkyl" with the following term -- $C_5$-$C_7$ cycloalkyl --.

Column 7, line 49, please replace the term "Raloxitene HCl" with the term -- Raloxifene HCl --.

Signed and Sealed this

Ninth Day of February, 1999

Attest:

Attesting Officer

*Acting Commissioner of Patents and Trademarks*